United States Patent [19]

Scharp et al.

[11] Patent Number: 4,868,121
[45] Date of Patent: Sep. 19, 1989

[54] ISLET ISOLATION PROCESS

[75] Inventors: David W. Scharp, St. Louis; Paul E. Lacy, Webster Groves; Edward H. Finke, Jennings; Thomas J. Poteat, Leslie, all of Mo.

[73] Assignees: McDonnell Douglas Corporation; Washington University, both of St. Louis, Mo.

[21] Appl. No.: 773,459

[22] Filed: Sep. 9, 1985

Related U.S. Application Data

[63] Continuation-in-part of Ser. No. 699,343, Feb. 27, 1985, abandoned.

[51] Int. Cl.⁴ .................. C07G 15/00; A01N 1/02
[52] U.S. Cl. ................................ 435/268; 435/1; 424/110
[58] Field of Search ................. 435/1, 268, 240; 424/110

[56] References Cited

PUBLICATIONS

Lacy et al., Diabetes, 31(8):109–111 (1982).
Scharp et al., J. Diabetes, 29(2):19–30 (1980) Suppl. 1.
Horaguchi et al., J. Surg. Res., 35:277–282 (1983).
Horaguchi et al., Diabetes, 30:455–458 (1981).
Shibata et al., Diabetes, 25(8):667–672 (1976).
Downing et al., Brief Comm., 29(1):79–83 (1980).
Scharp et al., Brief Comm., 16(6):686–689 (1973).
Sutherland et al., J. Surg. Res., 16:102–111 (1974).
Jakoby et al. (Eds), Methods In Enzymology, vol. LVIII, pp. 119–131, Academic Press, N.Y., 1979.
"An Immunological Approach to Islet Cell Purification," J. Cell Biol, 95:4061, 1982 Long et al.
"New Approaches in the Methods for Isolating Mammalian Islets of Langerhans Utilizing the Dog Pancreas," Chem Abstracts, 95:130315d, 1981, Scharp, et al.
"Method for Isolation of Islets of Langerhans from the Human Pancreas," Diabetes 33:1055, 1984, Gray et al.

*Primary Examiner*—Esther M. Kepplinger
*Attorney, Agent, or Firm*—Cohn, Powell & Hind

[57] ABSTRACT

A method of producing intact islets of Langerhans in an insulin producing condition uses a mixture of Hank's solution and 10% by volume fetal calf serum to ductally distend the human pancreas. The exocrine tissue of the pancreas is digested at about 37° C. by an enzyme preparation of collagenase, trypsin and proteolytic enzyme present in the mixture at a level of about 0.2% by weight. The digestion is monitored at regular intervals during the process. The digested pancreas is comminuted, filtered and intact islets of Langerhans are recovered. The recovered islets retain their insulin producing properties.

8 Claims, 9 Drawing Sheets

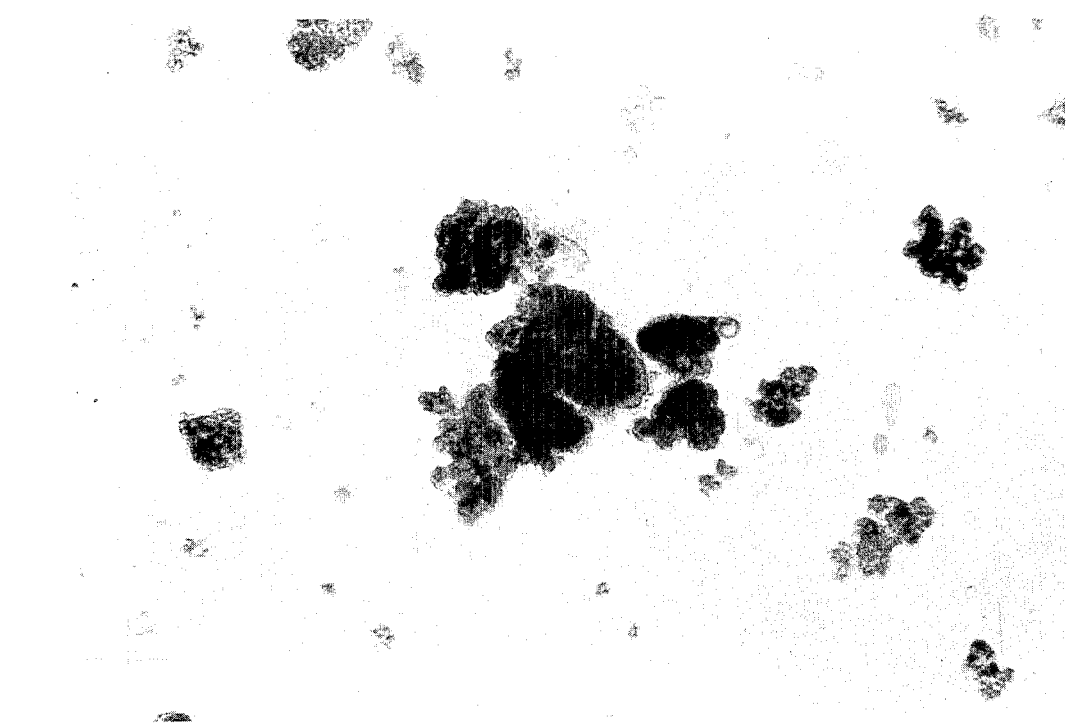
FIG. 2A  Under Digested  20X
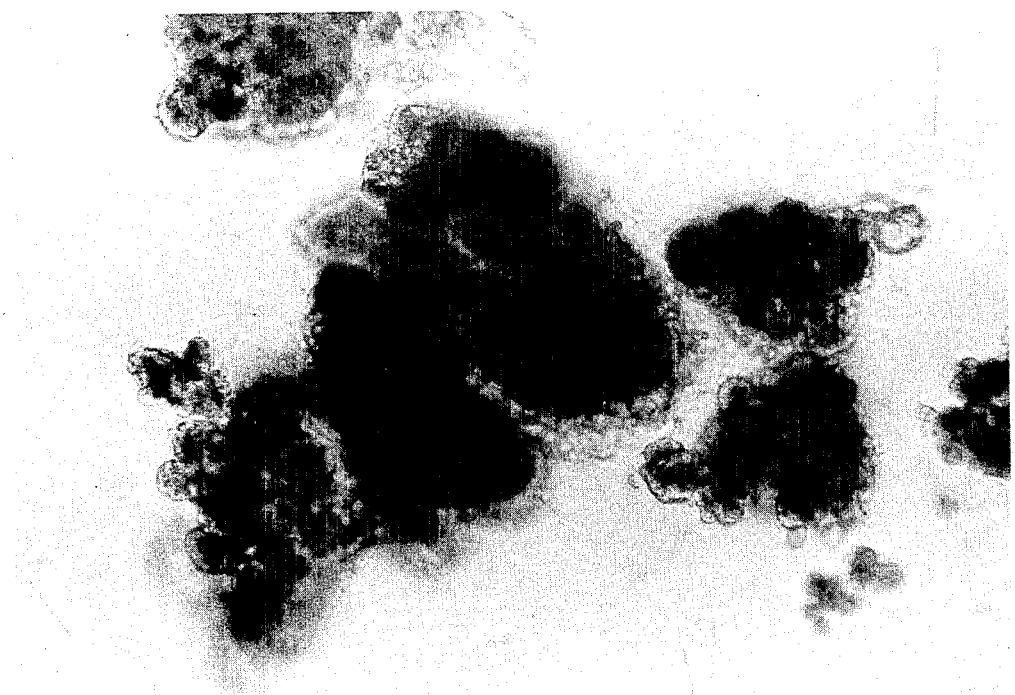
FIG. 2B  Under Digested  50X

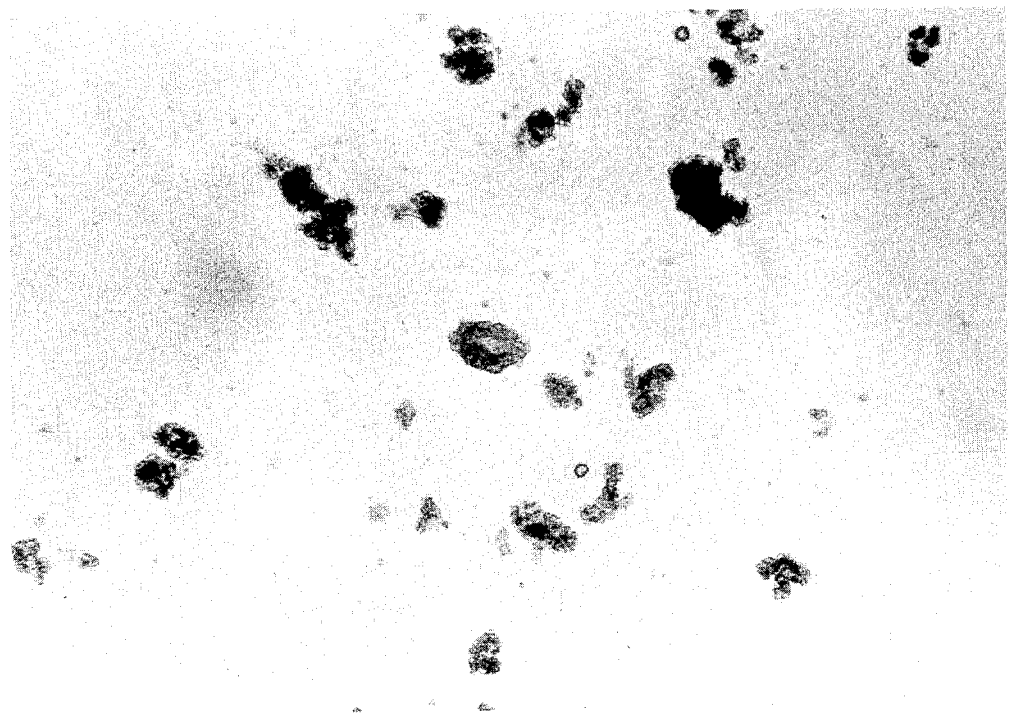
FIG. 3A  Over Digested  20X
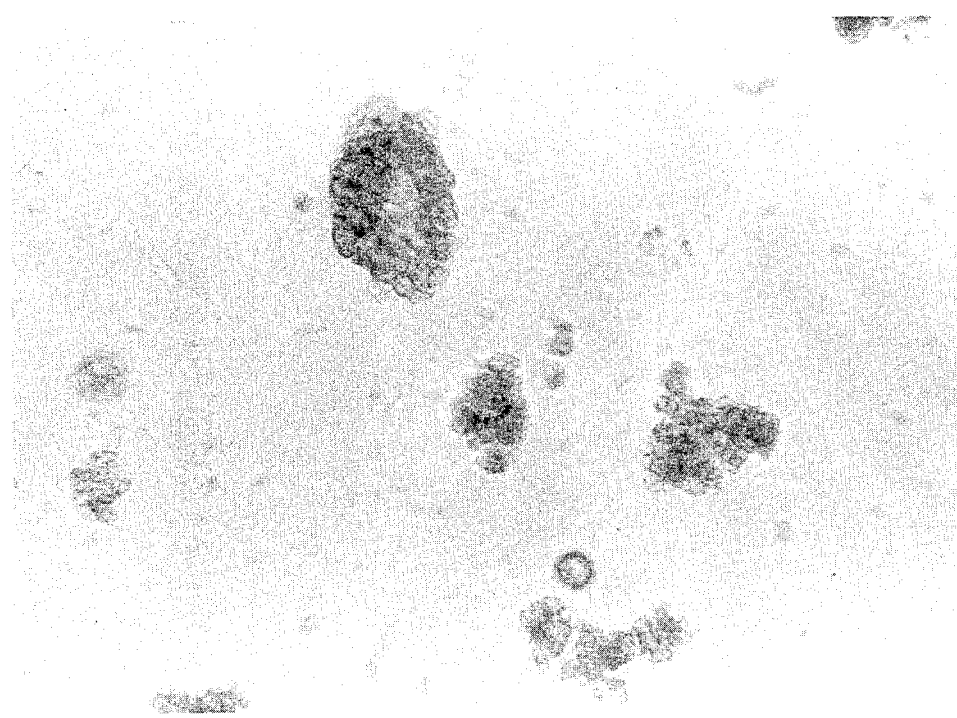
FIG. 3B  Over Digested  60X

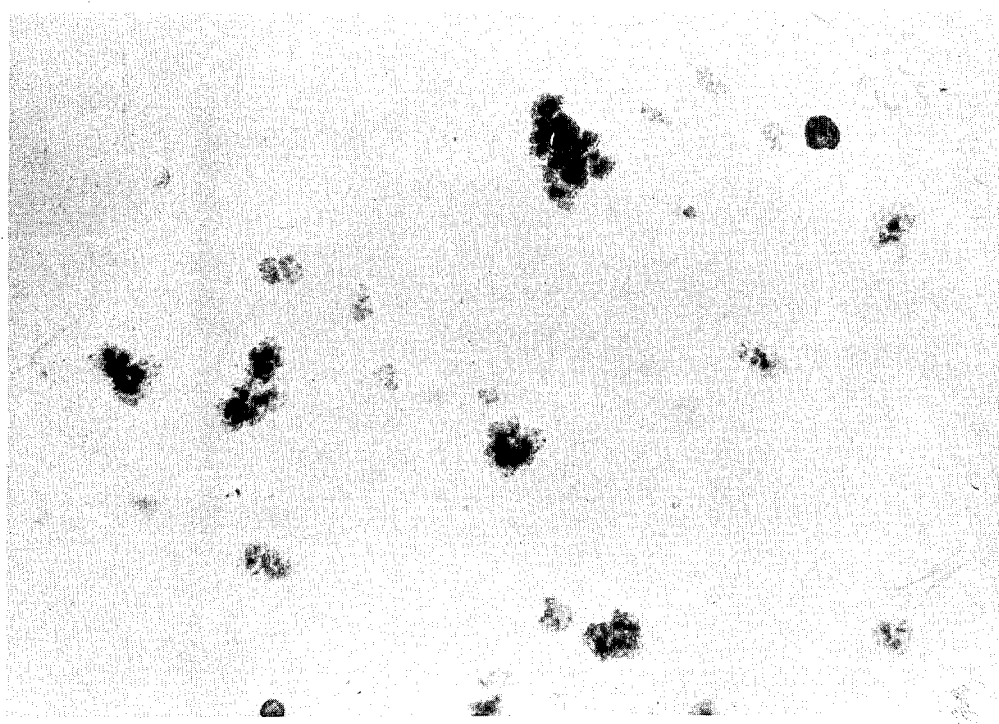
FIG. 4A Maximum Islet Separtion 20X
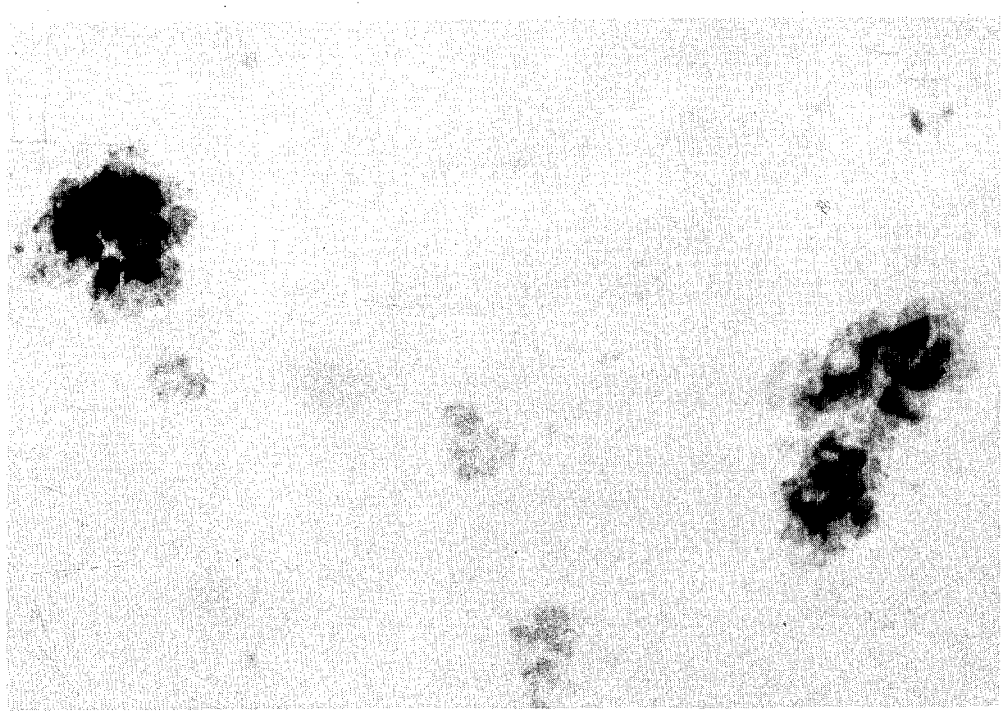
FIG. 4B Maximum Islet Separtion 50X

FIG. 8 Underdigested -- before islets are liberated.
The dark structure is partially digested pancreas.
50X
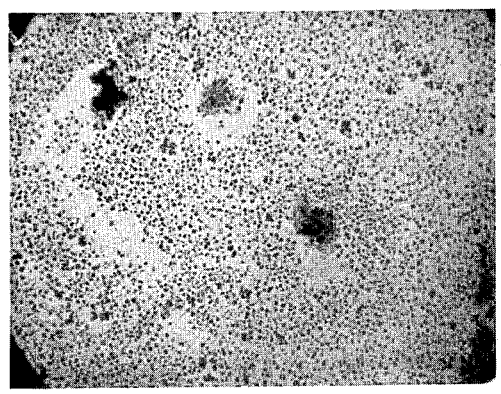
FIG. 9    Optimum digestion -- Free islets.
50X
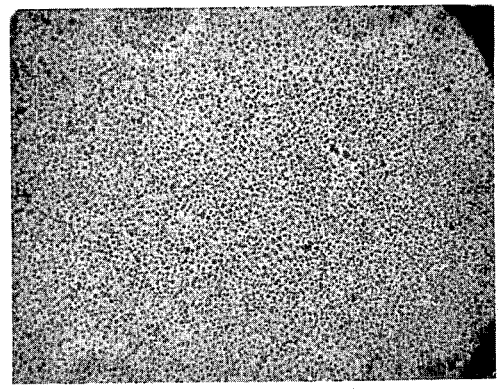
FIG. 10   Digested too long.
Only single cells are present.
50X 4,868,121

ISLET ISOLATION PROCESS

This application is a continuation-in-part of our prior application Serial No. 06/699,343, filed Feb. 27, 1985 now abandoned.

This invention relates to a method of isolating insulin producing elements from a pancreas.

BACKGROUND AND SUMMARY OF THE INVENTION

The insulin producing tissue of the pancreas, the islets of Langerhans, constitutes between about one and two percent of the mass of the pancreas. The isolation of the islets is desirable for laboratory purposes and for transplantation purposes. Transplantation of islets is looked to as a possible treatment for diabetes. Transplanting islets rather than segments of or an intact pancreas offers several advantages, including the ease of transplantation, the possibility of in vitro treatment to prevent rejection without immunosuppression, the elimination of the pancreatic exocrine function (the secretion of digestive substances from the host tissue), the possibility of cryopreservation of the tissue for subsequent use, and the possibility of xenografts.

The development and present state cf the art in islet separation and transplantation is thoroughly reviewed in Volume 8, No. 2 of the *World Journal of Surgery*, April 1984, incorporated herein by reference. Previous work on separating islets of the rat pancreas is reported in *The Journal of the American Diabetes Association*, Vol. 16, No. 1, pp. 35-39, "Method For the Isolation of Intact islets of Langerhans From the Rat Pancreas," Lacy, et al., also incorporated by reference herein. In the original method of islet separation, still in use today, chopped pancreatic fragments are mixed with collagenase and incubated at 37° C. until the maximum amount of islets are freed. The collagenase breaks down or digests the pancreas tissue, freeing the islets. The collagenase also acts on the islets, so that the islets released early in the process are broken down into single cells. If the process is stopped to protect the islets released early, many islets remain trapped in pancreatic fragments. Thus, only a fraction of the available intact islets are released by this method. This process is particularly ineffective for the isolation of islets from the pancreases of larger animals such as humans or dogs or pigs.

Laboratory islet isolation was greatly improved by the discovery that mechanical distension of rodent pancreas increased islet yield by causing mechanical separation of islets from the pancreas tissue. However, the same effect has not been noted in the pancreases of larger animals such as humans or dogs or pigs. After distension, the pancreas is chopped for collagenase digestion. This is presently accomplished by hand with scissors, which is unsatisfactory for mass processing, but mechanically powered chopping devices have been found to be too destructive to the islets.

Another variation of the collagenase isolation of islets is to wash the chopped pancreas fragments with an enzyme solution through a screen. This allows free islets to pass through the screen into a medium where they are protected from further enzyme activity.

Yet another technique employs Velcro TM fabric to hold the fibrous pancreas tissue while digesting it with the collagenase to release the islets.

All the present techniques for islet isolation, which are reviewed in Scharp, "Isolation and Transplantation of Islet Tissue," 8 *World Journal of Surgery* 143-151, 1984, incorporated herein by reference, are unsatisfactory for islet isolation, especially from the pancreases of larger animals. These techniques fall short in terms of efficiency of recovery and purity of the product. The procedures are simply inadequate for mass production techniques and the product is unsuitable for transplantation or other uses requiring purity.

The present invention is a new process for isolating the insulin producing tissue from a pancreas. The process involves ductal distension of the pancreas with a solution containing collagenase and incubating the pancreas at about body temperature, 37° C., until a satisfactory separation of islets is observed. The pancreas is then quartered and macerated. The macerated pancreas is forced through successively smaller screens to filter out the pancreas tissue from the freed islets. The islet material can then be purified with an elutriator or other filtering means. The resulting product contains islet fragments and pancreas particles, as well as whole, viable islets, however, the islet content is sufficient to meet the requirements for transplantation purposes.

This process isolates viable, purified islets from human pancreases and from the pancreases of other animals. The process makes xenografts, the transplantation of islets of Langerhans from other animals to humans, possible because it removes most of the other pancreatic tissue and thereby reduces the chances of rejection of the transplant. Xenografts are particularly important because of the limited availability of healthy human pancreases for experimentation and transplantation.

The inventors have discovered that pig pancreases are very similar to human pancreases. This process can be utilized to isolate viable islets of Langerhans from pig pancreases for experiment and transplantation into humans.

BRIEF DESCRIPTION OF THE DRAWINGS

FIG. 2 is a photomicrograph of a human pancreas sample treated under the process of this invention before the maximum islet separation has been reached;

FIG. 3 is a photomicrograph of a human pancreas sample treated under the process of this invention after the maximum islet separation has passed;

FIG. 4 is a photomicrograph of a human pancreas sample treated under the process of this invention at approximately the point of maximum islet separation;

FIG. 8 is a photomicrograph of a pig pancreas sample treated under the process of this invention before the maximum islet separation has been reached;

FIG. 9 is a photomicrograph of a pig pancreas sample treated under the process of this invention after the maximum islet separation has passed;

FIG. 10 is a photomicrograph of a pig pancreas sample, treated under the process of this invention at approximately the point of maximum islet separation;

DETAILED DESCRIPTION OF THE PREFERRED EMBODIMENT

The process of this invention is particularly suitable for the isolation of human islets which have heretofore been difficult to isolate in significant quantities. The process, of course, requires a pancreas. These organs are obtained from regular organ procurement channels. The organs, once removed from the deceased donor, are placed in a Eurocollins solution at 4° C. for preservation. The pancreas may be stored in this manner for as long as 24 hours prior to isolating the islets.

Figure 1:
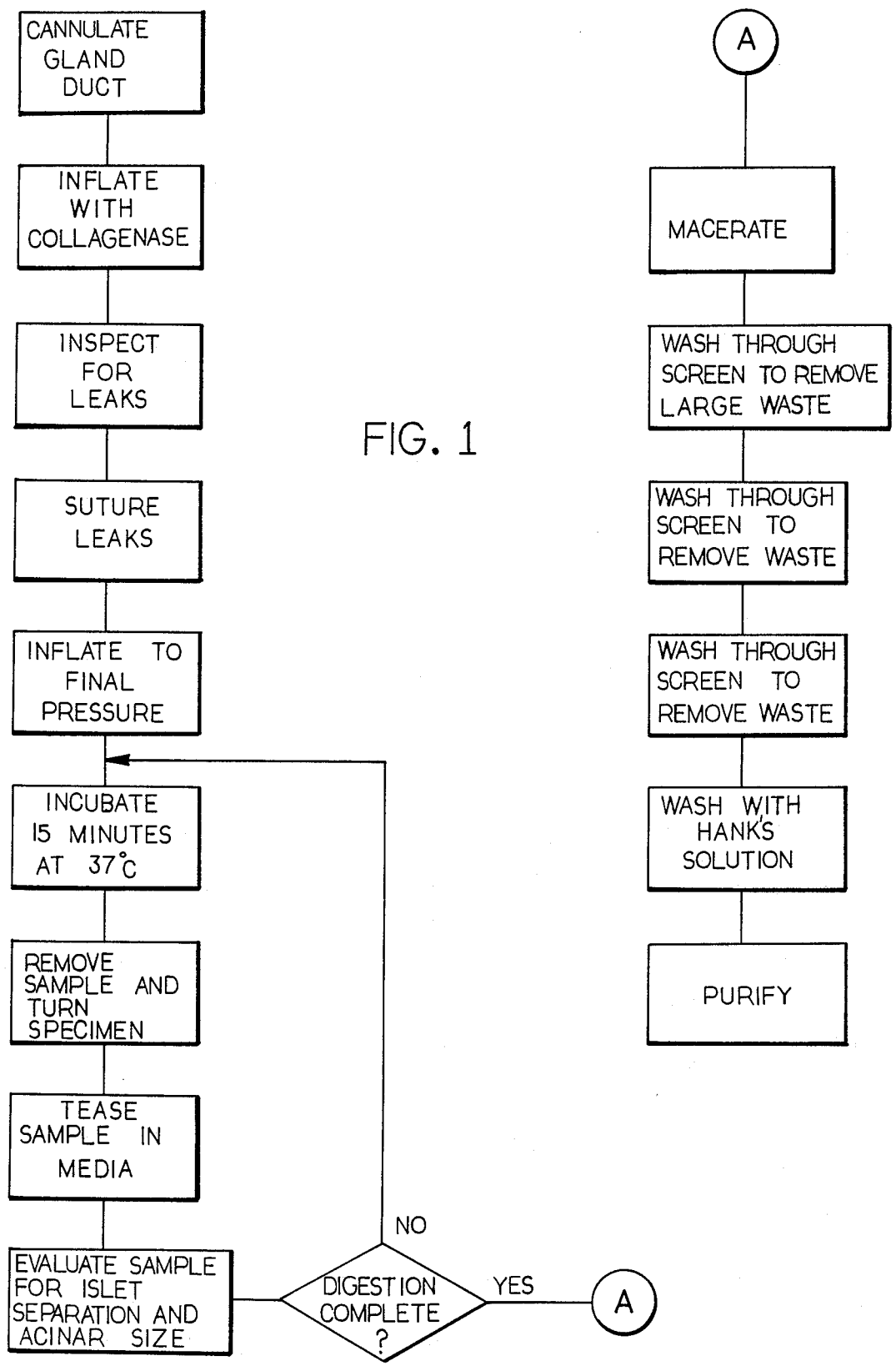
FIG. 1 is a schematic flow chart of the preferred embodiment of the process of islet separation of this invention.

The process is represented schematically in FIG. 1. The pancreas is cannulated with an 18 gauge angiocatheter inserted into the pancreatic duct and ligated. The pancreas is partially distended with Hank's solution containing 10 percent by volume fetal calf serum and 0.2 percent collagenase. It will be appreciated that these proportions are not critical, but greater or lesser amounts may be used and satisfactory results obtained. The pancreas is inspected for leaks, which are repaired by suturing. The pancreas is then fully inflated with a total of between about 150 and about 200 ml of liquid. Inflation or distension of the pancreas is believed to cause some mechanical rupturing of the exocrine tissue or partial separation of the islets from the exocrine tissue, making subsequent collagenase digestion easier. This physical disruption of the pancreas is important to islet isolation.

The Hank's solution used is a standard saline solution buffered by the addition of sufficient sodium bicarbonate to achieve a pH of 7.4, when in equilibrium with the $CO_2$ in room temperature air (20° C.). This solution is available from the Sigma Chemical Co., designated as Hank's balanced salts, H-8262, listed on page 858, in the 1984 Sigma Chemical Co. Catalog. The non-buffered Hank's solution is Sigma Chemical Co. number H-6136. The fetal calf serum is a heat inactivated serum, it also is standard, and can also be obtained from the Sigma Chemical Co., it is designated as Fetal Bovine serum F-2760, listed on page 859 in the 1984 Sigma Chemical Co. Catalog. The fetal calf serum can be obtained in a non-heat inactivated form from Sigma Chemical Co. as product number F-4884. The selection of the proper collagenase enzyme is empirical. It is expected that a number of collagenase preparations are suitable. One preparation of collagenase which is commercially available from Sigma Chemical Company, designated as C-3280, type V, listed on page 277 in the 1984 Sigma Chemical Catalog, has been found effective. Enzyme C-3280 is similar to enzymes C-9263 and C-0773, also available from Sigma Chemical Co. The difference being the degree of purity. Enzyme C-3280 is of a purity level greater than C-9263 but less than C-0773. It is believed that selected lots of C-9263 may also be effective in the process, if suitably screened as described herein. The enzyme preparation is the product of the fermentation of Clostridia histolyticum bacteria. The enzyme preparation listed herein contains a mixture of collagenase, trypsin and various proteolytic enzymes. Due to the nature of bacterial fermentation processes, the titer of the enzyme recovered from any given batch varies. Thus, not all of the above-identified collagenase preparation recovered is uniformly effective. To find a suitably effective lot, then, samples of several lots should be tested, by running trial digestions as described herein, to determine if they effectively digest the pancreas tissue. Of course, once an effective lot is identified, that entire lot can be used without additional testing.

At this time it is not understood precisely what in the enzyme preparation makes the preparation effective. A highly purified preparation of collagenase, however, has been found to be ineffective.

The inflated inoculated pancreas is immersed in a bath of Hank's solution containing 10% by volume fetal calf serum and 0.2% by weight collagenase and incubated at 37° C. At fifteen minute intervals a sample of approximately 30 $mm^3$ is taken. The sample is teased apart with forceps and examined under a phase microscope to determine the state of islet separation. While the incubation continues, the testing procedure continues at fifteen minute intervals until the maximum islet separation is observed. At this point large numbers of intact islets can be liberated by teasing the sample. This point is usually reached between about 45 minutes and about 90 minutes of incubation.

The determination of maximum islet separation is empirical, and experience is the best guide. If the incubation is stopped too early, a large portion of the islets remain trapped in the pancreas tissue. These islets will be destroyed, rather than liberated, in subsequent processing. FIG. 2 is a photomicrograph of a pancreas sample treated under this process before the maximum islet separation has been achieved. If the incubation process is stopped too late, the islets freed early in the incubation are digested into the individual cells. FIG. 3 is a photomicrograph of a pancreas sample treated under this process after the maximum islet separation had passed. In the optimally incubated pancreas, there will be approximately 100 islets visible in the teased 30 $mm^3$ sample. FIG. 4 is a photomicrograph of a pancreas sample under this process at approximately the point of maximum islet separation.

After the state of maximum islet separation is empirically determined, the pancreas is removed from incubation, quartered, and macerated. The combination of the mechanical disruption of the pancreas by the inflation and the enzyme digestion frees a sufficient number of islets to allow recovery of an effective islet concentrate. The islets are not destroyed in the subsequent maceration and separation process. This is in contrast to prior methods where manual fragmentation was required to preserve the islets. Maceration is satisfactorily accomplished in a meat grinder similar to a standard kitchen handgrinder, but mechanically powered, having ⅛ inch holes on the endplate. ⅛ inch holes have been empirically determined to be preferable over 1/16 inch holes and ¼ inch holes. The grinder macerates and shears the tissue, liberating the islets from the rest of the pancreas with minimal destruction of the whole islets.

The macerated pancreas is then washed with the Hank's solution described above. The washed macerated pancreas is collected in a beaker at 4° C. The pancreas tissue is washed through successively smaller screens with the Hank's solution to remove large waste particles. The first screen is preferably a 1 mm stainless steel screen. The second screen is preferably a 0.7 mm stainless steel screen. The final screen is preferably a 500 micron siliconized stainless steel screen. The filtrate, approximately 500 ml of dispersed, suspended material, is collected and is ready for purification. The purification step involves removal of toxic subcellular particles and pancreas tissue fragments. Several alternative purification methods may be used.

Figure 5:
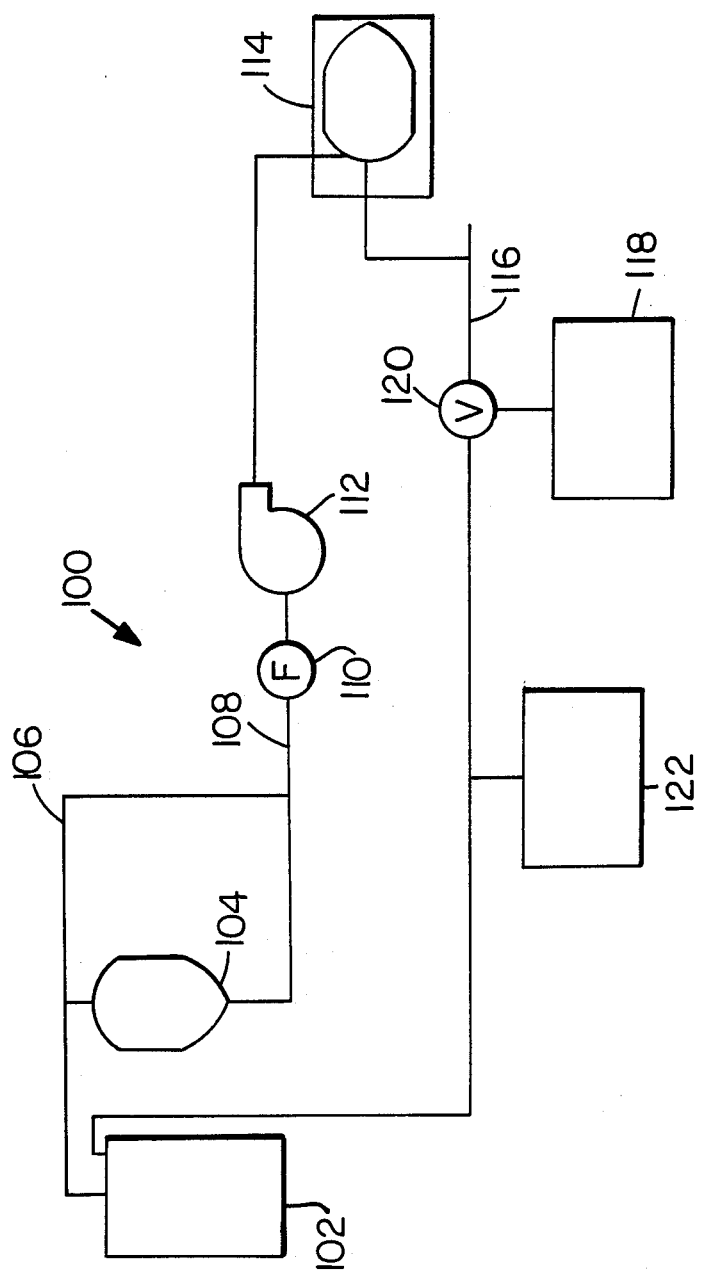
FIG. 5 is a schematic drawing of one purification system for purifying the islets separated by the process of this invention.

One purification system found effective for purifying the islet material is shown schematically in FIG. 5 as 100. System 100 comprises a reservoir 102 of a separator fluid (the Hank's solution) connected to a Teflon ™ coated separatory funnel 104 and a parallel bypass 106. Bypass 106 and the exit of funnel 104 are connected to line 108 containing flow meter 110 and pump 112. Line 108 leads to elutriator 114. Elutriator 114 can be the model JE-10X elutriator obtained from Beckman Instruments. The apparatus is adjusted to trap particles greater than 22 microns. The exit of elutriator 114 is connected to line 116 which contains a waste container 118, assessible via valve 120, and a product container 122. Line 116 returns to resevoir 102.

The approximately 500 ml of material resulting from the process is mixed with approximately 500 ml of the Hank's solution to reach approximately one liter, and transferred to funnel 104. Circulation is started in system 100 via bypass 106. Once circulation is established, funnel 104 is brought on line and material flows from funnel 104 through line 108, through flow meter 110, through pump 112, and into elutriator 114 where the relatively larger islets and islet sized particles are trapped. Smaller waste products (less than 22 microns) including toxic substances, enzymes, and single cells are trapped in waste container 118. Funnel 104 is preferably agitated during the process to achieve a more even flow of material. Once the material is completely filtered, the valve 120 to waste container 118 is closed, and elutriator 114 is backwashed, freeing the trapped islets and islet sized particles. These concentrated islets or islet sized particles are trapped in container 122. The product is washed with the Hank's solution and is ready for use, including transplantation.

Figure 6:
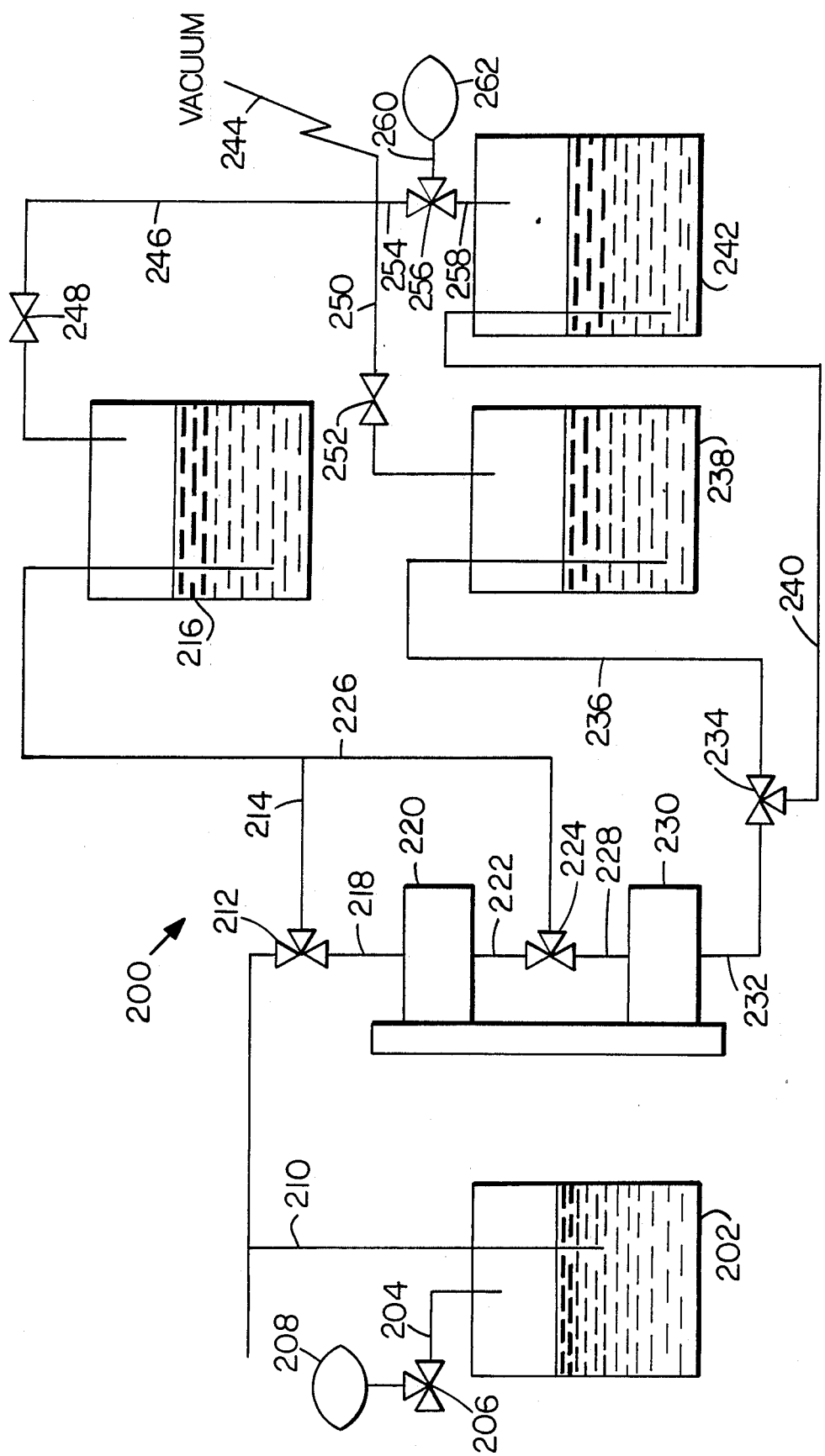
FIG. 6 is a schematic drawing of a second purification system for purifying the islets separated by the process of this invention.

A second system for purifying islet material is shown schematically in FIG. 6 as 200. System 200 comprises a container 202 for holding the islet material. Container 202 is vented with line 204 through valve 206 and filter 208. Line 210 connects container 202 to valve 212. Line 214 connects valve 212 to container 216 for recovering purified islets. Line 218 connects valve 212 to first filter 220. Line 222 connects filter 220 to valve 224. Line 226 connects valve 224 to container 216. Line 228 connects valve 224 to second filter 230. Filters 220 and 230 are operatively connected to shaker table 232 for vibrating filters 220 and 230.

Line 232 connects filter 230 to valve 234. Line 236 connects valve 234 to container 238 for collecting waste. Line 240 connects valve 234 to reservoir 242. Reservoir 242 contains Hank's solution and fetal calf serum for flushing the islets from the filters, as described below.

A vacuum source 244 is connected to islet collection container 216 with line 246, containing valve 248; to waste collection container 238 with line 250, containing valve 252; and, to valve 256 with line 254. Line 258 connects valve 256 to reservoir 242. Line 260 connects valve 256 to filter 262.

System 200 operates in two modes: a filter mode in which material in container 202 is filtered, and a recovery mode in which islets captured in filters 220 and 230 are flushed into container 216.

In the first mode, valves 248 and 256 are closed and valve 252 is opened so the vacuum 244 is applied to container 238. Reservoir 242 is not used in the filtrations so valve 234 is closed to line 240. Collection container 216 is also not used in the filtration so valve 224 is closed to line 226 and valve 212 is closed to line 214. The vacuum applied to container 238 draws material from container 202 through filters 220 and 230, which trap the islets and pass the filtrate which collects in container 238. This is continued until all the material in container 202 has been filtered. The vent line 204 and filter 208 allows the material to be drawn from container 202.

System 200 is then switched to the second mode. Valve 256 is opened to vent reservoir 242 with lines 260 and filter 262. Valve 252 is closed; and valve 248 is opened so the vacuum 244 is applied to container 216. Valve 212 is closed to the now empty container 202. Valve 234 is closed to waste container 238. Both valves 212 and 224 are opened to container 216 so that the vacuum applied to container 216 draws fluid from reservoir 242, through filters 220 and 230, flushing the islets trapped in filters 220 and 230 into container 216.

Figure 7:
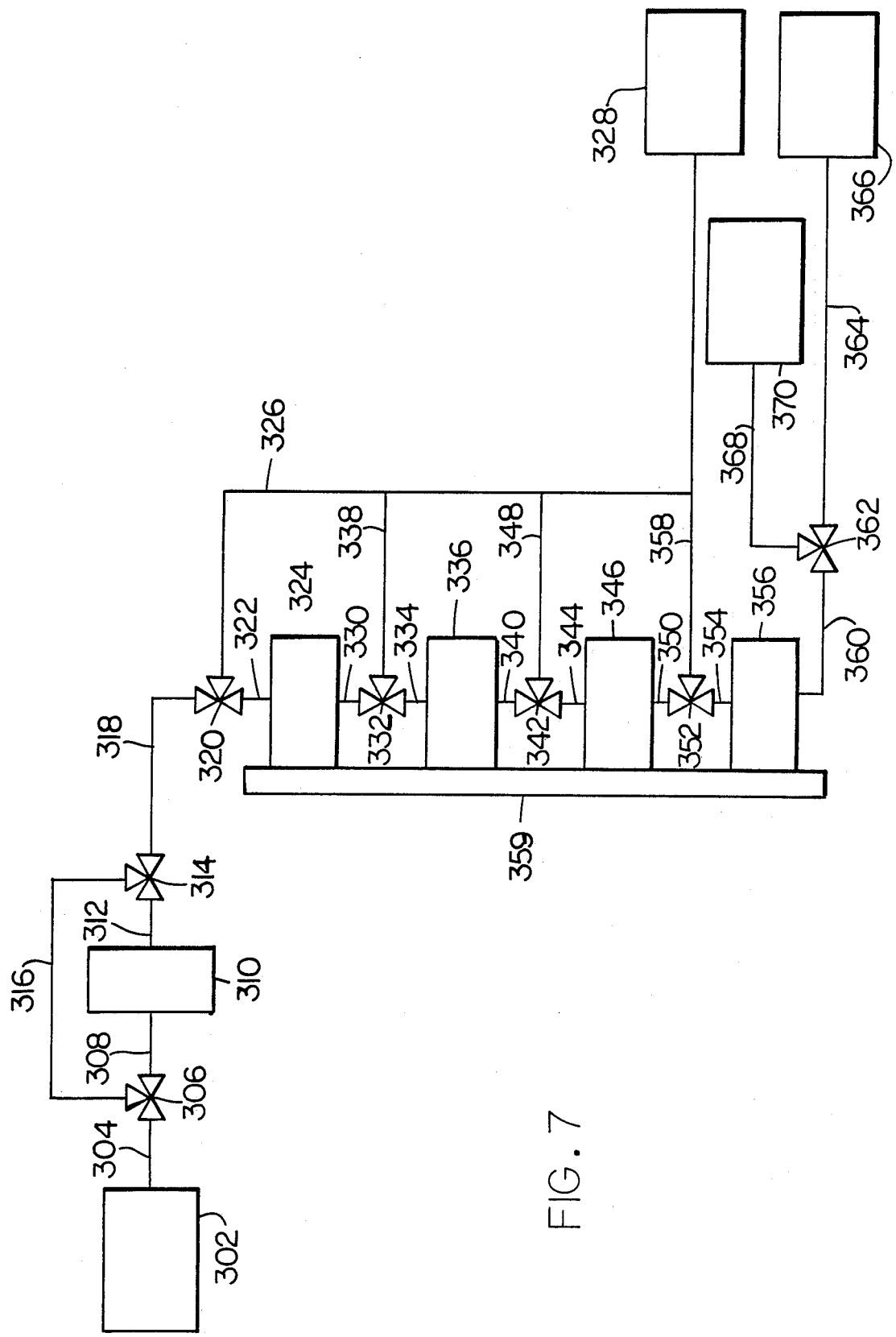
FIG. 7 is a schematic drawing of a third purification system for purifying the islets separated by the process of this invention.
Figure 11:
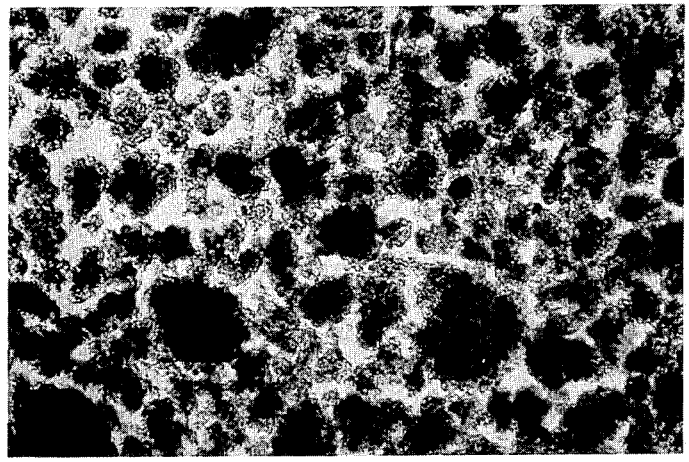
FIG. 11 is a photomicrograph of purified, isolated pig islets.

A third system for purifying islet material is shown schematically in FIG. 7 as 300. System 300 includes a container 302 for holding the islet material. Line 304 connects container 302 to valve 306. Line 308 connects container 302 to valve 306. Line 308 connects valve 306 to filter 310. Filter 310 is preferably a 500 micron Swinex filter. Line 312 connects filter 310 to valve 314. Bypass line 316 connects valve 306 to valve 314.

Line 318 connects valve 314 to valve 320. Line 322 connects valve 320 to filter 324. Line 326 connects valve 320 to container 328 for collecting islets. Line 330 connects filter 324 to valve 338. Line 334 connects valve 332 to filter 336. Line 338 connects valve 320 to container 218. Line 340 connects filter 336 to valve 342. Line 344 connects valve 342 to filter 346. Line 348 connects valve 342 to container 328. Line 350 connects filter 346 to valve 352. Line 354 connects valve 352 to filter 356. Line 358 connects valve 352 to container 358. Filters 324, 336, 346, and 356 are in descending order of size, and are all smaller than filter 310. They are preferably Swinex filters in the following sizes: 324–250 micron; 336–150 micron; 346–100 micron; and 356–53 micron. Filters 324, 336, 346, and 356 are operatively connected to shaker table 359 for vibrating the filters.

Line 360 connects filter 356 to valve 362. Line 364 connects valve 362 to container 366 for collecting waste. Line 368 connects valve 362 to reservoir 370. Reservoir 370 contains Hank's solution and fetal calf serum for flushing the islets from the filters, as described below.

System 300 operates in two modes a filter mode in which material in container 302 is filtered, and a recovery mode in which islets captured in filters 324, 336, 346, and 356 are flushed into container 328. In the first mode valves 306 and 314 are only closed to bypass line 316. Valve 320 is only closed to line 326. Valve 332 is only closed to line 338. Valve 352 is only closed to line 358. Valve 352 is only close to line 358. Valve 362 is only closed to line 368 (reservoir 370). Either a pump can be activated to pump the islet material from container 302 through system 300 or a vacuum can be applied to container 366 to draw material from container 322. The islet material passes through filter 310 and then successively through filters 324, 336, 346, and 356, which trap the islets and pass the filtrate, which collects in waste container 366.

Once all the islet material is filtered, system 300 is switched to its second mode. Valve 362 is closed to line 364 and opened to line 368, bringing reservoir 370 on line. Valve 320 is closed to line 318. Either a pump can be activated to pump fluid from reservoir 370 or a vacuum can be applied to container 328 to draw the liquid from reservoir 370. Each of filters 356, 346, 336, and 324 are then flushed in seriatum by closing the valve above the filter to the line leading to the preceding filter and opening the valve to the line leading to container 328. The valve is returned to normal and the next larger filter is flushed in the same manner until each of filters 356, 346, 336, and 324 has been flushed and their contents collected in container 328.

The product from any of the purification processes contains fragments of islets and islet sized fragments of pancreas in addition to whole, viable islets, but the resultant product is anticipated to be sufficiently pure for transplantation and experimentation. Approximately 40% of the islets are recovered by this process. This is well over the 20% believed to be sufficient to provide adequate insulin production. Thus, the process yields sufficient islets from just one pancreas for transplantation.

A measure of successful operation of the process is in comparison of the RIA (Radioimmune assay) values for insulin in the pancreas and in the product. Insulin values of the product should be at least 25% of the original value in the pancreas and preferably between about 30% and about 35%. The following table shows the yields from islet separation of human pancreases using the process of this invention and a comparitive test of a modified process performed without ductal distension. Item 4 in the table is a test performed on a human pancreas which had the ducts cut when the pancreas was removed. The pancreas could not be inflated, so the pancreas was immersed in the enzyme mixture and digested prior to islet recovery.

volume fetal calf serum and maintained at about 4° C. for preservation. The pancreas may be stored in this manner for as long as 4-6 hours prior to the isolation process. The pancreas is promptly transported to the laboratory for islet isolation.

The process is represented schematically in FIG. 1. The pancreas is prepared by cutting across the neck of the pancreas to separate the tail. Preferably only the tail of the pancreas is used for islet isolation. The tail of the pancreas is cannulated with a 20 gauge angiocatheter inserted into the pancreatic duct and ligated. The pancreas is placed in a double-walled stainless steel vessel. Hot water can be circulated between the double walls of the vessel to incubate the pancreas as described below.

A collagenase solution is prepared by dissolving 200 mg of a suitable collagenase such as C-3280, type V, from Sigma Chemical Co. described above in 200 ml of Hank's solution containing 10% by volume fetal calf serum. Other suitable collagenase preparations can be used and these can be identified as described above. This solution is maintained at about 24° C. Although preferable, these proportions are not critical, and greater or lesser amounts may be used and satisfactory results obtained.

The solution is injected with a syringe into the pancreatic duct of the pancreas via the angiocatheter to inflate and distend the pancreas. Leaks are sutured. As with the human pancreas, the inflation or distension of the pancreas is believed to cause some mechanical rupturing of the exocrine tissue or partial separation of the islets from the exocrine tissue, making subsequent collagenase digestion easier. In any event this physical disruption of the pancreas is important to islet isolation. External fat, connective tissue, and blood vessels are trimmed from the pancreas.

TABLE I

HUMAN ISLET ISOLATION

| NO. | INSULIN CONTENT PANCREAS (UNITS) | INSULIN CONTENT ISLETS (UNITS) | INSULIN % YIELD | ESTIMATED NO. OF ISLETS |
|---|---|---|---|---|
| 1 | 308 | 93 | 30% | 66,600 |
| 2 | 314 | 117 | 37% | 56,000 |
| 3 | 116 | 76 | 66% | 10,000 |
| 4 | 454 | 23 | 5% | 8,250 |
| 5 | 306 | 184 | 60% | 120,000 |
| 6 | 607 | 184 | 30% | 26,950 |
| 7 | 678 | 153 | 23% | 79,500 |
| 8 | 160 | 64 | 40% | 15,525 |
| 9 | 391 | 144 | 37% | 118,250 |
| 10 | 132 | 40 | 30% | 25,000 |
| 11 | 523 | 328 | 63% | 90,000 |
|   |   |   | 42% |   |

It is anticipated that purity of product can be further improved through use of the electrophoresis process described in "Electrophoresis Chamber," U.S. Pat. No. 4,310,408, the specification of which is incorporated by reference herein.

The process of this invention can also be used to isolate islets of Langerhans from the pancreas of a donor animal. One suitable donor animal is the pig. The process is substantially the same as the isolation of islets of Langerhans from a human pancreas. The Hank's solution, the fetal calf serum, and the collagenase are of the same type as described in detail above with regard to the isolation of human islets.

The pancreas is removed from the pig carcass preferably within 15 minutes after the pig is killed. The pancreas is placed in the Hank's solution containing 10% by The inflated pancreas is then immersed in a bath of collagenase solution similar to that injected into the pancreatic duct. The pancreas is incubated at about 37° C. in the double walled stainless steel vessel described above. At 4 minute intervals a sample of approximately 30 mm$^3$ is taken. The sample is teased apart with forceps and examined under a phase microscope to determine the state of islet separation. While the incubation continues, the testing procedure continues at four minute intervals until the maximum islet separation is observed. At this point large numbers of intact islets can be liberated by teasing the sample. This point is usually reached between about 12 and about 16 minutes of incubation.

The determination of maximum islet separation is empirical, and experience is the best guide. If the incubation is stopped too early, a large portion of the islets remain trapped in the pancreas tissue. These islets will be destroyed, rather than liberated, in subsequent processing. FIG. 8 is a photomicrograph of a pancreas sample treated under this process before the maximum islet separation has been achieved. If the incubation process is stopped too late, the islets freed early in the incubation are digested into individual cells. FIG. 9 is a photomicrograph of a pancreas sample treated under this process after the maximum islet separation had passed. In the optimally incubated pancreas, there will be approximately 25-50 islets visible in the teased 30 mm³ sample. FIG. 10 is a photomicrograph of a pancreas sample under this process at approximately the point of maximum islet separation.

After the state of maximum islet separation is empirically determined, the pancreas is immediately placed in 300 ml of Hank's solution containing 10% by volume of fetal calf serum at 4° C. The cold solution is used to stop further digestion of the pancreas. The pancreas is cut into large pieces and these pieces are macerated. Maceration is satisfactorily accomplished in the same grinder described above for the processing of human pancreas. The grinder macerates and sheers the tissue, liberating the islets from the rest of the pancreas with minimal destruction of the whole islets.

The macerated pancreas is then washed with the Hank's solution described above. The washed and macerated pancreas is collected in a beaker of Hank's solution at 4° C. The pancreas tissue is washed through successively smaller screens with the Hank's solution to remove large waste particles. The first screen is preferably a 1 mm stainless steel screen. The second screen is preferably a 0.7 mm stainless steel screen. The final screen is preferably a 500 micron siliconized stainless steel screen. These are the same types of screens used in the isolation of human islets described above. The filtrate, approximately 1000 ml of dispersed, suspended material, is collected and is ready for purification. A larger amount of Hank's solution is used to disperse the pig pancreas than the human pancreas because the pig pancreas will rapidly digest itself unless diluted. The purification step involves removal of toxic subcellular particles and pancreas tissue fragments.

The inventors have developed a purification method well suited for the purification of islet bearing filtrate resulting from the digestion of animal pancreases. The approximately 1000 ml of filtrate containing the digested pancreatic tissue is placed in six flat bottom, 250 ml, plastic centrifuge tubes and centrifuged at about 500 rpm for about two minutes at about 4° C. The supernatant is poured off and the tissue pellet is resuspended by the addition of about 30 ml of Hank's solution containing 10% by volume fetal calf serum at 4° C. to each tube, and the contents of each tube is divided equally into eight round-bottom, 50 ml, glass centrifuge tubes.

These tubes are centrifuged at about 400 X G for about thirty seconds at about 4° C. The supernatant is again poured off leaving a tissue pellet in each centrifuge tube.

The islets are purified using the Ficoll gradient centrifugation method that has been used for the separation of rat islets as described in Lindall, H., Steffes, M. & Sorenson, R., *Endocrinology*, Vol. 85 at page 218 (1969), incorporated herein by reference. Ficoll is a monionic synthetic polymer of sucrose with a molecular weight of approximately about 400,000. Ficoll is commercially available from Sigma Chemical Co., designated as F9378 on page 446 of the 1985 Sigma Chemical Co. Catalog. The procedure involves suspending the tissue pellet in each of the 50 ml centrifuge tubes in 6 ml of 25% Ficoll. Three additional layers of decreasing concentrations of Ficoll are layered on top of the 25% Ficoll layer in each tubes. These Ficoll layers are respectively, 4 ml of 23% Ficoll, 4 ml of 20.5% Ficoll, and 4 ml of 11% Ficoll. The Ficoll gradients are centrifuged at about 800 X G for about 10 minutes at about 4° C. The islets form a distinct band at the first Ficoll interface between the 11% and 20.5% layer and a less distinct band at the second interface between the 20.5% and the 23% layer. The two bands are removed separately with a pipette and washed two times in succession with the Hank's solution containing 10% by volume fetal calf serum, by centrifugation, in order to remove the Ficoll. The first band between the 11% and 20.5% of Ficoll layers contains nearly all of the islets. Experiments have shown that the first band contains approximately 84% of the islets and the second band contains only about 16% of the islets. This is illustrated by the data in Table II. As shown in the last column of Table II recoveries appear to exceed 100% because the large pig islets often breakdown into a plurality of smaller viable islets.

The islets obtained from the Ficoll gradient purification are intact and the purity of the preparation is approximately 95% islets with the remainder being small pancreatic ducts and small clumps of acinar cells. Experiments have shown that the isolated islets are viable and functional after this isolation and purification. As shown in Table III, the mean insulin secretion of islets separated was $0.923 \pm 0.15$ $\mu$ units/islet/minute in the presence of non-stimulatory levels of glucose and increased to $2.20 \pm 0.25 \mu$ units/islet/minute when the glucose was raised to a stimulatory level. Table II indicates that massive numbers of islets can be successively isolated from pig pancreas by method described and the islets are morphologically and functionally intact. Pig islets isolated by this procedure can be used either for basic studies on insulin secretion, for insulin production or extraction, or for islet transplantation, or for encapsulation in artificial membranes prior to transplantation.

TABLE II

| Pig No. | Pancreas Wt. (Gms) | Waste Wt (Gms) | Islet No. Filtrate | Islet No. 1st Ficoll Band | Islet No. 2nd Ficoll Band | Total No. Isolated Islets | Isolated Islets Per Gram Pancreas | % Recovery |
| --- | --- | --- | --- | --- | --- | --- | --- | --- |
| 97 | 64.47 | 11.87 | 122,000 | 88,900 | 12,050 | 100,950 | 1,919 | 82.7 |
| 95 | 89.19 | 1.67 | 59,000 | 55,350 | 11,850 | 67,200 | 768 | 113.0 |
| 94 | 92.84 | 4.05 | 56,000 | 32,250 | 5,100 | 37,350 | 421 | 66.6 |
| 93 | 73.34 | 5.46 | 74,000 | 66,050 | 15,200 | 81,250 | 1,197 | 109.0 |
| 92 | 97.30 | 11.21 | 122,000 | 58,300 | 6,650 | 64,950 | 754 | 53.0 |
| 91 | 97.41 | 5.73 | 95,000 | 176,850 | 8,500 | 185,350 | 2,022 | 195.0 |
| 90 | 84.56 | 7.90 | 100,000 | 51,040 | 21,120 | 72,160 | 942 | 72.1 |
| 89 | 69.35 | 8.08 | 94,000 | 35,200 | 26,800 | 62,000 | 1,012 | 65.9 |
| 88 | 66.11 | 12.09 | 60,000 | 48,900 | 14,100 | 63,000 | 1,166 | 105.0 |
| 87 | 91.03 | 18.60 | 149,000 | 69,250 | 23,650 | 92,900 | 1,283 | 62.3 |

TABLE II-continued

| Pig No. | Pancreas Wt. (Gms) | Waste Wt (Gms) | Islet No. Filtrate | Islet No. 1st Ficoll Band | Islet No. 2nd Ficoll Band | Total No. Isolated Islets | Isolated Islets Per Gram Pancreas | % Recovery |
|---|---|---|---|---|---|---|---|---|
| 86 | 84.46 | 13.80 | 96,000 | 107,475 | 5,250 | 112,707 | 1,595 | 117.4 |
| 85 | 82.70 | 18.61 | 95,000 | 139,800 | 4,550 | 144,350 | 2,252 | 152.0 |
| 84 | 38.80 | 7.86 | 82,000 | 61,000 | 8,100 | 69,100 | 2,234 | 84.0 |
| Ave. | 79.35 | 9.76 | 92,620 | 76,182 | 12,532 | 88,713 | 1,351 | 98.3 |

TABLE III

IN VITRO SECRETION OF INSULIN BY ISOLATED PIG ISLETS

| Pig No. | Glucose 3 mM Insulin $\mu$Units/Islet/Minute | Glucose 28 mM Insulin $\mu$Units/Islet/Minute |
|---|---|---|
| 70 | 0.25 | 0.66 |
|  | 0.09 |  |
|  | 0.31 | 0.64 |
|  | 0.26 | 0.58 |
| 71 | 0.85 | 3.01 |
|  | 0.21 | 1.35 |
| 76 | 1.60 | 2.58 |
|  | 1.70 | 2.82 |
| 77 | 0.61 | 2.46 |
|  | 0.78 | 2.50 |
|  | 1.09 | 1.74 |
| 79 | 1.70 | 2.93 |
|  | 1.72 | 2.10 |
|  | 1.72 | 3.15 |
| 80 | 0.77 | 3.17 |
|  | 1.36 | 2.11 |
|  | 0.67 | 4.31 |
| Mean $\pm$ SEM | 0.923 $\pm$ 0.15 | 2.20 $\pm$ 0.25 |

$P < 0.001$

There are various changes and modifications which may be made to the inventors' invention, as would be apparent to those skilled in the art. However, any of these changes or modifications are included in the teaching of the inventors' disclosure and they intend that the invention be limited only by the scope of the claims appended hereto.

We claim:

1. The method of recovering intact islets of Langerhans from pancreas comprising ductally distending an intact pancreas with a mixture of Hank's solution and 10% by volume fetal calf serum containing 0.2% by weight of an enzyme preparation containing collagenase, and incubating the pancreas to digest the exocrine tissue of the pancreas, monitoring the pancreas at regular intervals during the digestion to empirically determine the point of maximum islet separation, the combination of physical disruption of the distension and the enzymatic digestion being effective to free viable islets of Langerhans from the pancreatic tissue while retaining the insulin producing properties of the islets, removing the intact islets from the remaining pancreatic tissue and digested product and recovering the intact islets of Langerhans in their insulin producing condition, the recovery being performed by first chopping the digested pancreas and macerating the digested pancreas by mechanical grinding, the grinding being effective to reduce the size of the pancreatic tissue to about the size of an intact islet while retaining the maximum number of islets in their whole, insulin producing condition, and second, separating the intact islets from the exocrine tissue of the pancreas by filtration and concentration, the recovered concentrate containing intact islets in a condition effective to produce insulin.

2. The method of claim 19 wherein the pancreas is distended with between about 150 and about 200 ml of the mixture.

3. The method of claim 19 including partially distending the pancreas, checking for leaks, suturing the leaks closed and fully distending the pancreas for incubation.

4. The method of claim 19 wherein the step of filtration and concentration comprises washing the macerated pancreatic tissue through a series of successively smaller screens with Hank's solution to remove particles larger than about 500 microns.

5. The method of claim 4 wherein the step of filtration and concentration includes a second filtration, the second filtration comprising washing the once filtered pancreatic tissue through a series of successively smaller filters, the smallest being about 53 microns, with Hank's solution and backwashing the filters with Hank's solution and fetal calf serum to recover the filtered islets.

6. The method of claim 1 wherein a human pancreas is used and the pancreas is digested for between about 45 and about 90 minutes.

7. The method of claim 1 wherein a pig pancreas is used and wherein the pancreas is digested for between about 14 and 16 minutes.

8. A process for isolating intact islets from a pancreas, comprising the steps of ductally distending the pancreas with a solution containing collagenase and incubating the pancreas in a solution containing collagenase until an effective separation of islets from the other pancreatic tissue is observed;

chopping the pancreas into large fragments and macerating the large fragments by mechanical grinding, the grinding being effective to reduce the size of the pancreatic tissue to about the size of an intact islet while retaining the islets in their whole condition;

forcing the macerated pancreas fragments through successively smaller screens to filter the other pancreatic tissue from the islets;

and purifying the islets.

* * * * *